United States Patent

Cricchio et al.

[11] 4,002,752
[45] Jan. 11, 1977

[54] PIPERAZINYLIMINO RIFAMYCINS

[75] Inventors: Renato Cricchio, Varese; Vittorio Arioli, Como, both of Italy

[73] Assignee: Gruppo Lepetit, S.p.A., Milan, Italy

[22] Filed: Feb. 26, 1976

[21] Appl. No.: 661,587

[30] Foreign Application Priority Data

Mar. 25, 1975 United Kingdom ............ 10020/75

[52] U.S. Cl. .................. 424/250; 260/239.3 P
[51] Int. Cl.[2] ................... C07D 491/08
[58] Field of Search .......... 260/239.3 P; 424/250

[56] References Cited

UNITED STATES PATENTS 3,342,810   9/1967   Maggi et al. ............. 260/239.3 P Primary Examiner—Henry R. Jiles
Assistant Examiner—Robert T. Bond
Attorney, Agent, or Firm—Theodore Post; C. Kenneth Bjork

[57] ABSTRACT

Novel rifamycins characterized by the following structural formula

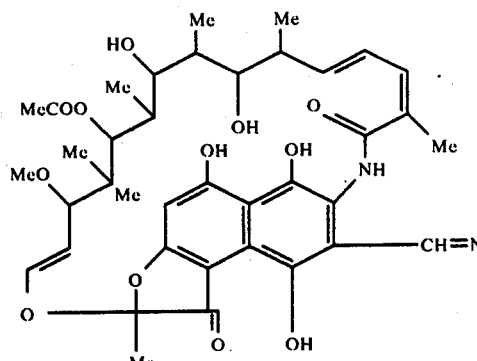

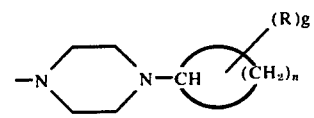

wherein Me represents a methyl group, $n$ represents 3, 4, 5 or 6; $g$ represents 0, 1 or 2; and each R represents a lower alkyl group selected from methyl or ethyl substituting for a hydrogen atom of a —$CH_2$— group; and wherein, when $g$ is 2, the two lower alkyl groups may replace hydrogen atoms of two different methylene groups as well as hydrogen atoms of the same methylene group. The compounds of this invention possess a broad spectrum antibacterial utility accompanied by a low toxicity.

8 Claims, No Drawings

PIPERAZINYLIMINO RIFAMYCINS

BACKGROUND OF THE INVENTION

Some condensation products of 3-formylrifamycin SV with aminopiperazines are described in U.S. Pat. No. 3,342,810. Among the compounds therein described, the condensation product of 4-methyl-1-aminopiperazine with 3-formylrifamycin SV (rifampicin) has found wide application in chemotherapy against infectious diseases and, particularly, against tuberculosis and leprosy.

In the prior literature, there are reported no condensation derivatives of 3-formylrifamycin SV with 1-aminopiperazines having a cycloalkyl substituent in the 4-position.

SUMMARY OF THE INVENTION

This invention relates to novel compounds of the rifamycin family. The new compounds are characterized by the following structural formula

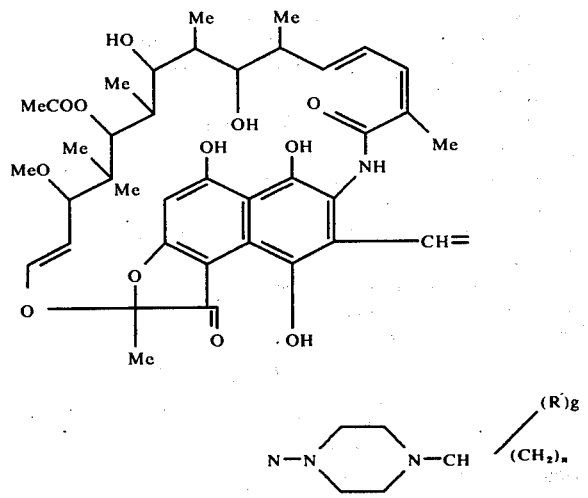

wherein Me represents a methyl group; $n$ represents 3, 4, 5 or 6; $g$ represents 0, 1 or 2; and each R represents a lower alkyl group selected from methyl or ethyl substituting for a hydrogen atom of a $-CH_2-$ group; and wherein, when $g$ is 2, the two lower alkyl groups may replace hydrogen atoms of two different methylene groups as well as hydrogen atoms of the same methylene group.

The compounds of this invention possess a broad spectrum antibacterial utility accompanied by a low toxicity.

DESCRIPTION OF SOME PREFERRED EMBODIMENTS

The novel rifamycins are prepared by condensing 3-formylrifamycin SV with an aminopiperazine of the formula

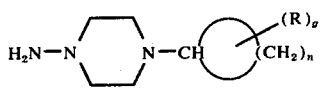

wherein $n$, $g$ and R have meanings given above. In the reaction, the 3-formylrifamycin SV is contacted with a substantially equimolar proportion (and preferably a 0.1 molar excess) of the predetermined aminopiperazine in the presence of an inert organic solvent such as, for instance, dioxane, tetrahydrofuran, methanol, ethanol, benzene or ethyl acetate. The temperature of the reaction ranges from ambient temperature to reflux temperature of the reaction mixture. The reaction is generally followed by thin layer chromatography. After completion of the reaction, the solvent is distilled off under reduced pressure and the residue is purified by crystallization from a solvent or by column chromatography. Suitable solvents for crystallization are the lower alkanols, ethyl acetate, hexane or mixtures thereof.

The synthesis of the aminopiperazine reactants is accomplished by following known procedures which involve alkylation of N-nitroso piperazine with an appropriate cycloalkyl bromide or chloride followed by reduction of the nitroso group with $LiAlH_4$ to obtain the corresponding amino derivative. An alternative route involves nitrosation of an N-cycloalkylpiperazine followed by reduction of the nitroso group with $LiAlH_4$.

Examples of compounds falling within the scope of the invention, which are prepared according to the processes above described, are those of formula I wherein the substituents at the piperazine nitrogen in the 4-position represented by the partial formula

are the following: cyclobutyl, cyclopentyl, cyclohexyl, cycloheptyl, 2-methylcyclobutyl, 3-methyl-cyclobutyl, 3,3-dimethylcyclobutyl, 2,2-dimethylcyclobutyl, 2-methylcyclopentyl, 3-methylcyclopentyl, 3-ethylcyclopentyl, 3-methylcyclohexyl, 4-methylcyclohexyl, 2-methylcyclohexyl, 4-ethylcyclohexyl, 2-ethylcyclohexyl and 3,5-dimethylcyclohexyl.

The following additional description and examples further describe the invention and the manner and process of making and using it to enable the art skilled to make and use the same and set forth the best mode contemplated by the inventors of carrying out the invention.

EXAMPLE 1

3-(4-Cyclopentyl-1-piperazinyl)iminomethylrifamycin SV 0.01 Mole of 3-formylrifamycin SV is dissolved in tetrahydrofuran and to the obtained solution 0.011 mole of 1-amino-4-cyclopentylpiperazine is added to the reaction mixture at room temperature. After 30 minutes, the reaction is completed since thin layer chromatography of the mixture shows disappearance of the starting 3-formylrifamycin SV. The solvent is then evaporated off and the residue is crystallized from ethyl acetate. The title product, which melts at 179°–80° C, is obtained in a 55% yield.

The spectrophotometric data are the following:

| λmax (mμ) | ε |
|---|---|
| 475 | 15,200 |
| 334 | 26,700 |

The elementary analysis is in agreement with the theoretical values. The starting 1-amino-4-cyclopentylpiperazine (b.p. 80°–82° C/0.1 mm Hg) is obtained by alkylating N-nitrosopiperazine with cyclopentyl bromide in ethanol in the presence of $NaHCO_3$ and reducing the so-obtained 1-nitroso-4-cyclopentylpiperazine with $LiAlH_4$ in ethyl ether.

EXAMPLE 2

3-(4-Cyclobutyl-1-piperazinyl)iminomethylrifamycin SV

The title compound is obtained in a 50% yield by following the procedure of Example 1 and employing 1-amino-4-cyclobutylpiperazine instead of 1-amino-4-cyclopentylpiperazine. The title product melts at 165°–68° C (crystallized from ethyl acetate).

The spectrophotometric data are the following:

| $\lambda$max (m$\mu$) | $\epsilon$ |
|---|---|
| 470 | 17,500 |
| 333 | 30,500 |

The elementary analysis is in agreement with the theoretical values. The starting 1-amino-4-cyclobutylpiperazine is obtained according to the same procedure followed for 1-amino-4-cyclopentylpiperazine. The product is utlized in the crude state.

Other compounds which are prepared according to the procedure described in the foregoing examples are:

3-[4-(2-methylcyclobutyl)-1-piperazinyl]iminomethylrifamycin SV 3-(4-cyclohexyl-1-piperazinyl)iminomethylrifamycin SV 3-[4-(3-methylcyclopentyl)-1-piperazinyl]iminomethylrifamycin SV 3-[4-(3,4-dimethylcyclopentyl)-1-piperazinyl]iminoethylrifamycin SV 3-[4-(3,3-dimethylcyclobutyl)-1-piperazinyl]iminomethylrifamycin SV 3-[4-(3-methylcyclobutyl)-1-piperazinyl]iminoethylrifamycin SV 3-[4-(3-ethylcyclobutyl)-1-piperazinyl]iminomethylrifamycin SV 3-[4-(2,2-dimethylcyclobutyl)-1-piperazinyl]iminoethylrifamycin SV 3-[4-(3-ethylcyclobutyl)-1-piperazinyl]iminomethylrifamycin SV 3-[4-(4-methylcyclohexyl)-1-piperazinyl]iminomethylrifamycin SV 3-[4-(3-methylcyclohexyl)-1-piperazinyl]iminomethylrifamycin SV 3-[4-(3,5-dimethylcyclohexyl)-1-piperazinyl]iminomethylrifamycin SV 3-(4-cycloheptyl-1-piperazinyl)iminomethylrifamycin SV 3-[4-(2-methylcyclohexyl)-1-piperazinyl]iminoethylrifamycin SV 3-[4-(4-ethylcyclohexyl)-1-piperazinyl]iminoethylrifamycin SV The novel rifamycin products, besides possessing the usual broad spectrum activity which is peculiar to this class of compounds, are characterized by the fact that they also show a remarkable therapeutic effectiveness in treatments with administration schedules allowing unusually large intervals of time between successive administrations of the active substance. This lasting property offers considerable advantages in therapeutic practice, since it allows one to obtain good results without the need of daily administration. In experiments carried out with the novel rifamycins on mammals such as mice, one or two administrations per week have shown the same or better effectiveness than daily administration of the same dose leve of rifampicin. The necessity of a frequent administraton schedule, such as a daily schedule, to obtain a reliable therapeutic effect, besides the disadvantage of needing a large amount of biologically active substance during the whole therapy cycle, undoubtedly represents for the patients a troublesome task, in particular in a long term ambulatory therapy with, for example, rifampicin.

The unexpected biological characteristics of the novel rifamycins have been evidenced by considering the survival time after a daily administration of rifampicin in comparison with a once a week administration of the same dose level per os of 3-(4-cyclopentyl-1-piperazinyl)iminomethylrifamycin SV (hereinafter referred to as "cyclopentyl derivative") to mice infected with Mycobacterium tuberculosis $H_{37}R_v$. The mice treated with the cyclopentyl derivative showed about the same survival time although each of them did actually receive a total amount of the active substance which was about one-sixth of the total amount of active substance received by each of the animals undergoing a rifampicin regimen.

The novel rifamycins, besides the abovementioned lasting properties, possess a very good antimicrobial activity and a low toxicity. For instance, the value of the minimal inhibitory concentration in vitro of the cyclopentyl derivative against Mycobacterium tuberculosis $H_{37}R_v$ is 0.05 $\mu$g/ml, while that of rifampicin is 0.5 $\mu$g/ml. The $LD_{50}$ of the cyclopentyl derivative in mice is higher than 2000 mg/kg p.o. and 750 mg/kg i.p., while the corresponding values for rifampicin are, respectively, 907 and 416.

The outstanding effectiveness and safety of the new rifamycins in combatting microbial infections has been proved also in experimental Staphylococcus aureus infections in mice. In fact, the "cyclobutyl derivative" (i.e. 3-(4-cyclobutyl-1-piperazinyl)iminomethylrifamycin SV) in representative experiments has shown an $ED_{50}$ value of 0.16 mg/kg p.o. The toxicity is very low, since the $LD_{50}$ value in mice is higher than 2000 mg/kg p.o. and 650 mg/kg i.p.

The new compounds are suitably administered in ways usual with other rifamycins, using conventional pharmaceutical carriers.

We claim:

1. A rifamycin compound of the formula

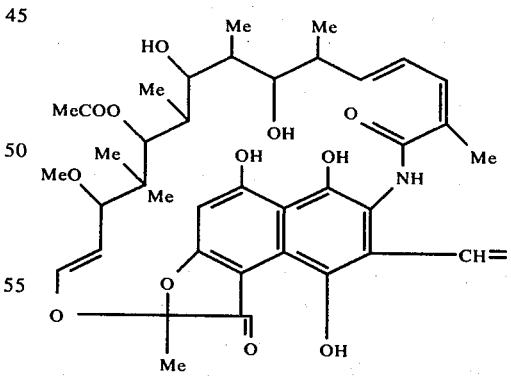

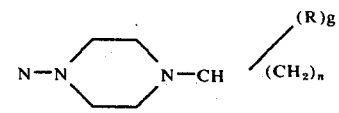

wherein Me represents a methyl group; $n$ represents the integer 3, 4, 5 or 6; $g$ represents the integer 0, 1 or 2; and each R represents a lower alkyl group selected from methyl or ethyl substituting for a hydrogen atom of a —$CH_2$— group.

2. A compound as claimed in claim 1 wherein n represents the integer 3 or 4.

3. The compound of claim 2 which is 3-(4-cyclopentyl-1-piperazinyl)iminomethylrifamycin SV.

4. The compound of claim 2 which is 3-(4-cyclobutyl-1-piperazinyl)iminomethylrifamycin SV.

5. A method for combatting a microbial infection in mammals which comprises administering to the infected mammal once or twice a week a therapeutically effective amount of a rifamycin compound as claimed in claim 1.

6. The method of claim 5 wherein the microbial infection is provoked by a *Mycobacterium tuberculosis* strain.

7. The method of claim 5 wherein the microbial infection is provoked by the strain *Mycobacterium tuberculosis* $H_{37}R_v$.

8. A pharmaceutical composition for combatting microbial infections containing an antimicrobially effective amount of a compound of the formula

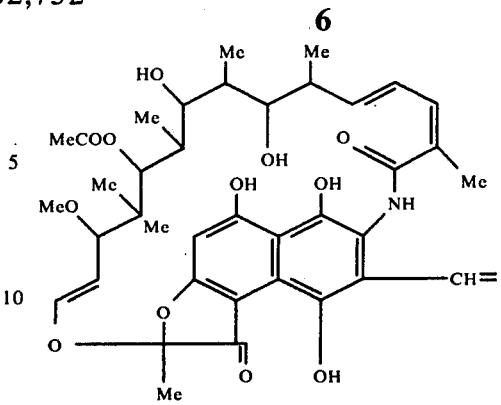

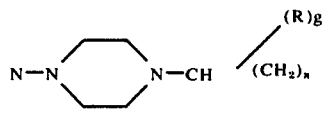

wherein Me represents a methyl group; n represents the integer 3, 4, 5 or 6; g represents the integer 0, 1 or 2; and each R represents a lower alkyl group selected from methyl or ethyl substituting for a hydrogen atom of a —CH₂— group admixed with a pharmaceutical carrier.

* * * * *

UNITED STATES PATENT OFFICE
CERTIFICATE OF CORRECTION

Patent No. 4,002,752              Dated January 11, 1977

Inventor(s) Renato Cricchio et al.

It is certified that error appears in the above-identified patent and that said Letters Patent are hereby corrected as shown below:

The structural formula as printed in the following places; i.e., - upper right side of the title page,
- Column 1, lines 22 through 42,
- Column 4, lines 45 through 65, and
- Column 6, lines 1 through 19 should read as follows:

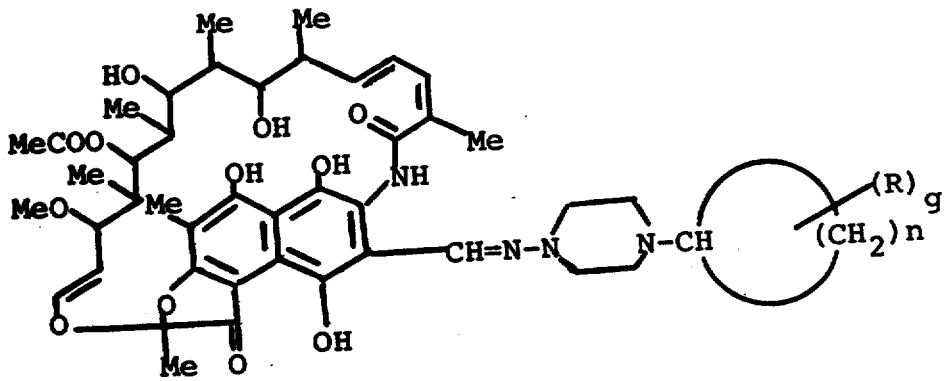

Column 1, line 66, after n, g and R have, add the missing word "the".

UNITED STATES PATENT OFFICE
CERTIFICATE OF CORRECTION

Patent No. 4,002,752          Dated January 11, 1977

Inventor(s) Renato Cricchio et al.

It is certified that error appears in the above-identified patent and that said Letters Patent are hereby corrected as shown below:

Column 3, line 21, "product is utlized" should read -- product is utilized --.

Column 3, line 67, "dose leve" should read -- dose level --; and line 68, "administraton" should read -- administration --.

Signed and Sealed this

Seventh Day of June 1977

[SEAL]

Attest:

RUTH C. MASON
Attesting Officer

C. MARSHALL DANN
Commissioner of Patents and Trademarks